United States Patent [19]

Frank et al.

[11] Patent Number: 5,318,772
[45] Date of Patent: Jun. 7, 1994

[54] ORAL COMPOSITIONS FOR INHIBITING CALCULUS FORMATION

[75] Inventors: R. Keith Frank; Joseph R. Garlich, both of Lake Jackson; Jaime Simon, Angleton; Garry E. Kiefer, Lake Jackson; David A. Wilson, Richwood, all of Tex.

[73] Assignee: The Dow Chemical Company, Midland, Mich.

[21] Appl. No.: 805,600

[22] Filed: Dec. 10, 1991

[51] Int. Cl.$^5$ ............................ A61K 7/16; A61K 7/22
[52] U.S. Cl. ........................................ 424/49; 424/54; 424/57
[58] Field of Search ...................................... 424/49–58

[56] References Cited

U.S. PATENT DOCUMENTS

| | | |
|---|---|---|
| Re. 29,182 | 4/1977 | McCune et al. |
| 3,488,419 | 1/1970 | McCune et al. |
| 3,860,576 | 1/1975 | Ham et al. |
| 3,925,456 | 12/1975 | Ploger et al. ............ 424/54 |
| 3,941,772 | 3/1976 | Ploger et al. ............ 424/54 |
| 3,960,888 | 6/1976 | Ploger et al. ............ 424/49 |
| 3,984,543 | 10/1976 | Ploger et al. ............ 424/54 |
| 3,988,443 | 10/1976 | Ploger et al. ............ 514/91 |
| 4,001,212 | 1/1977 | Richman. |
| 4,034,086 | 7/1977 | Ploger et al. ............ 514/91 |
| 4,054,598 | 10/1977 | Blum et al. ............ 424/54 |
| 4,064,164 | 12/1977 | Blum et al. |
| 4,098,880 | 7/1978 | Gaffar. |
| 4,100,270 | 7/1978 | Gaffar. |
| 4,108,961 | 8/1978 | Ploger et al. ............ 424/57 |
| 4,108,962 | 8/1978 | Ploger et al. ............ 424/57 |
| 4,118,474 | 10/1978 | Gaffar et al. |
| 4,123,512 | 10/1978 | Gaffar. |
| 4,137,303 | 1/1979 | Gaffar et al. |
| 4,161,518 | 7/1979 | Wen et al. |
| 4,168,265 | 9/1979 | Tabushi et al. |
| 4,174,428 | 11/1979 | Tabushi et al. |
| 4,177,258 | 12/1979 | Gaffar et al. |
| 4,183,915 | 1/1980 | Gaffar et al. |
| 4,215,105 | 7/1980 | Gaffar et al. |
| 4,224,308 | 9/1980 | Gaffar et al. |
| 4,224,309 | 9/1980 | Gaffar et al. |
| 4,273,579 | 6/1981 | Gaffar et al. |
| 4,348,381 | 9/1982 | Gaffar et al. |
| 4,459,241 | 7/1984 | Wilson et al. |
| 4,493,771 | 1/1985 | Wilson et al. |
| 4,540,508 | 9/1985 | Wilson et al. |
| 4,568,467 | 2/1986 | Crump et al. |
| 4,575,456 | 3/1986 | Hayes. |
| 4,627,977 | 12/1986 | Gaffar et al. |
| 4,663,154 | 5/1987 | Ryan. |
| 4,680,396 | 7/1987 | Crump et al. |
| 4,749,561 | 7/1988 | Lane et al. |
| 4,770,791 | 9/1988 | Crump et al. |
| 4,799,995 | 1/1989 | Crump et al. |
| 4,808,401 | 2/1989 | Gaffar et al. |
| 4,816,245 | 3/1989 | Gaffar. |
| 4,820,507 | 4/1989 | Klueppel et al. |
| 4,915,937 | 4/1990 | Amjad. |

FOREIGN PATENT DOCUMENTS

| | | |
|---|---|---|
| 0208009A1 | 1/1987 | European Pat. Off. |
| 0363748A2 | 4/1990 | European Pat. Off. |
| 480811 | 4/1992 | European Pat. Off. ............ 424/57 |
| 492998 | 7/1992 | European Pat. Off. ............ 424/57 |
| 9200721 | 1/1992 | PCT Int'l Appl. ............ 424/57 |
| 2210264A | 6/1989 | United Kingdom. |
| 2210265A | 6/1989 | United Kingdom. |

*Primary Examiner*—Shep Rose

[57] ABSTRACT

Oral compositions containing an effective amount as an anticalculus agent at least one cyclic alkylamine or cyclic amine in the presence or absence of a cationic antimicrobial agents.

6 Claims, 6 Drawing Sheets

ORAL COMPOSITIONS FOR INHIBITING CALCULUS FORMATION

BACKGROUND OF THE INVENTION

The present invention relates to oral compositions containing an anticalculus agent.

"Oral composition" means a composition for topical applications to the oral cavity to clean and care for the teeth as well as the oral cavity surfaces. Representatives of such compositions are oral hygiene products and dentifrices such as mouthwashes or rinses, toothpaste, dental gels, tooth powder, chewing gum, lozenges, and similar products. In addition to cleaning teeth to remove dental plaque, the function of oral hygiene preparations is to stop the formation of dental calculus, to prevent dental disorders such as caries, periodontitis and gingivitis, and also to eliminate halitosis.

Dental calculus, or tartar as it is sometimes called, is a hard mineralized material which forms on teeth that consists of inorganic and organic components. The inorganic portion is largely calcium and orthophosphate arranged in a crystal lattice called hydroxyapatite (HAP). The organic portion is derived mainly from microorganisms (i.e., bacteria, yeast, etc.) as well as epithelial cells, white blood cells and food debris.

Formation of dental calculus occurs in two steps. In the first step, plaque is deposited on the teeth. "Plaque" consists of inorganic and organic components derived from saliva, food and bacteria which are present in the oral cavity. Most of the plaque consists of dead and living bacteria surrounded by a gel-like matrix derived from the bacteria and saliva. In the second phase, plaque undergoes calcification to form dental calculus. Initially, amorphous deposits of calcium phosphate begin to appear on and within the matrix of the dental plaque. As the aggregates of calcium phosphate become sufficiently closely packed together, they crystallize to form HAP. The amorphous calcium phosphate, although related to hydroxyapatite, differs from it in crystal structure, particle morphology and stoichiometry.

The presence of both the bacteria and the plaque deposits is detrimental to the health of the teeth and gums. If the bacteria and the plaque formation are not checked, they may result in infected gingival tissue, the formation of dental caries and periodontal disease.

A wide variety of chemical and biological agents have been suggested in the art to retard calculus formation or to remove calculus after it is formed. Mechanical removal of this material periodically by the dentist is, of course, a routine dental office procedure.

Inhibition of oral bacteria involved in the formation of plaque by antibiotics or antiseptic agents is one means to retard the formation of calculus; see, for example, P. S. Hull, *J. Clinical Periodontology* 7, 431–442 (1980). Examples of antiseptic agents include bisbiguanides, such as chlorhexidine and alexidine, and numerous antibacterially active quaternary ammonium compounds, such as cetylpyridinium chloride or the quaternary ammonium compounds described in U.S. Pat. Nos. 3,369,046 and 4,820,507; and quaternary ammonium organosiloxane compounds described in U.S. Pat. No. 4,161,518.

Although the quaternary ammonium compounds are rapidly adsorbed onto the tooth surface, they exhibit only a moderate degree of efficacy as antiplaque agents as they are rapidly released from the tooth surface and thus retained in the oral cavity for only a short period of time. Chlorhexidine has been the most successful antiplaque agent and is retained in the oral cavity by binding to anionic groups mainly on the oral mucosa. The use of chlorhexidine in oral preparations however, suffers from the following disadvantages: (1) a prolonged bitter aftertaste lasting up to several hours; (2) with prolonged use stains are produced on the teeth, tongue, gums, oral mucosa and dental restorations; and (3) local irritation of the oral mucosa and tongue.

Another means to prevent plaque and calculus formation is to coat the teeth with a material to prevent the release of previously applied therapeutic agents or to coat the teeth with a material containing an antimicrobial agent. U.S. Pat. Nos. 4,243,658; 4,428,930; 4,470,964 and 4,485,090 disclose a dentifrice composition containing a water-dispersible, membrane-forming material which, when applied to tooth surfaces, forms a hydrophobic barrier thereon which substantially reduces elution of a previously applied therapeutic agent. A varnish containing an antimicrobial agent, which provides the sustained release of the antimicrobial agent over a period of at least four days was disclosed in U.S. Pat. No. 4,496,322. The use of the therapeutic agent or varnish coating is not entirely satisfactory as their application requires a qualified professional, making their use as part of routine oral hygiene maintenance impractical.

As the formation of calculus requires the crystallization of HAP, agents which effectively interfere with crystalline materials, including HAP, will be effective as anticalculus agents. Inhibition of crystalline HAP formation is therefore usually achieved by compounds which chelate calcium ions, which prevents the calculus from forming and/or breaks down mature calculus by removing calcium. It is known in the prior art that water-soluble hexametaphosphates, tripolyphosphates and pyrophosphates and the like, are effective calcium and magnesium ion threshold agents, sequestrants and/or chelating agents. A threshold agent has the ability to prevent the precipitation of certain scale forming salts (e.g., calcium carbonate) at concentrations that are much lower than the amount needed for sequestration. See, for example, U.S. Pat. No. 3,488,419, which discloses oral compositions containing polyphosphonate, and U.S. Pat. No. 4,215,105, which discloses oral compositions containing phosphonoacetic acid. The effectiveness of polyphosphonates as anticalculus agents has been limited as they are significantly hydrolyzed by salivary enzymes (phosphatases) to orthophosphates, which are ineffective as inhibitors of HAP formation. The amount of enzymatic hydrolysis of the polyphosphate has been reduced by the use of a linear molecularly dehydrated polyphosphate salt combined with fluoride as described in U.S. Pat. No. 4,808,410.

It is the object of the present invention to provide improved anticalculus oral compositions which inhibit the transformation of amorphous calcium phosphate to HAP crystal structure normally associated with calculus.

Another object of this invention is the provision of an improved method for inhibiting the formation of calculus in the oral cavity.

SUMMARY OF THE INVENTION

The present invention relates to an oral composition containing an anticalculus agent. In particular, the present invention relates to an oral composition comprising an orally-acceptable vehicle containing therein an effective amount as an anticalculus agent a cyclic alkylamine or a cyclic amine selected from one or more of the compounds represented by the formulae I to IV:

wherein each R is independently hydrogen, hydrocarbon radical having from 1-8 carbon atoms, hydroxyalkyl (wherein the alkyl group contains 2-6 carbon atoms), or wherein Z is independently —PO$_3$H$_2$, —COOH, —H, C$_1$-C$_{18}$ alkyl or a physiologically acceptable salt of the acid radicals; and X and Y are independently —H, or hydrocarbon radicals having from 1 to 3 carbon atoms;

with the further proviso that each cyclic alkylamine or cyclic amine has at least two Z groups which are —PO$_3$H$_2$, or a physiologically acceptable salt thereof;

each n within the ring is independently 2 or 3; and m is 3 to 6 inclusive;

n and m being selected such that the total number of carbon and nitrogen atoms in the cyclic amine ring does not exceed 18.

As used herein the term "alkyl" means a linear or branched alkyl and thus secondary and tertiary alkyls are included. The alkyl terms up to C$_{20}$ include, for example, t-butyl, sec-butyl, isobutyl, and in like manner all such branched or straight chain alkyls.

A further embodiment of the invention provides an oral composition which inhibits the transformation of amorphous calcium phosphate to the hydroxyapatite crystal structure normally associated with calculus.

In yet another embodiment of the present invention, there is provided an improved method of inhibiting the formation of dental calculus.

DETAILED DESCRIPTION OF THE INVENTION

This invention relates to an oral composition containing in an orally-acceptable vehicle an effective amount of an anticalculus cyclic amine or cyclic alkylamine. An "orally-acceptable vehicle" means a medium in which an anticalculus agent may be administered to the oral cavity without substantial harmful effects to the oral cavity surfaces. An "effective amount" is an amount that will inhibit the formation of calculus in the oral cavity.

Cyclic alkylamines of the present invention are derivatives of bicycloheptadiene as given in Formula (I)

or derivatives of dicyclopentadiene as given in Formula (II)

wherein each R is independently -H; hydrocarbon radical having from 1-8 carbon atoms; hydroxyalkyl (wherein the alkyl group contains 2-6 carbon atoms); or wherein Z is independently —PO$_3$H$_2$, -COOH, -H, C$_1$-C$_{18}$ alkyl or a physiologically acceptable salt of the acid radicals; and X and Y are independently -H, or hydrocarbon radicals having from 1 to 3 carbon atoms;

with the proviso that each cyclic alkylamine has two Z groups which are —PO$_3$H$_2$, or a physiologically acceptable salt thereof. A physiologically acceptable salt refers to the acid addition salts of those bases which will form a salt which does not cause a significant adverse physiological effect when used in an oral product consistent with good pharmacological practice. Examples of physiologically acceptable salts include those of the alkali and alkaline-earth metal salts and mixtures thereof.

Methods for preparing compounds of Formulae I-III are known in the art and reference made thereto for the purpose of this invention. For example, the cyclic alkylamines of Formulae I and II can be prepared from commercially available dicyclopentadiene (DCPD) and bicycloheptadiene (BCHD). Electrophilic addition reactions are known to form the nitrile or dinitrile by reacting the double bonds of DCPD or BCHD with hydrogencyanide (HCN). The nitrile can then be hydrolyzed to form the carboxylic acid derivative. The DCPD or BCHD can also be reacted with HCN followed by reduction to obtain the bis(methylamine) derivative; this product in turn can be reacted with glycolonitrile in the presence of caustic to give the sodium salt of the tetraacetic acid of the bisamine.

Cyclic amines of the present invention are macrocyclic amines of Formula (III):

(III)

or Formula (IV):

(IV)

wherein each n is independently 2 or 3 and m is 3 to 6, inclusive, n and m being selected such that the total number of carbon and nitrogen atoms in the cyclic amine ring does not exceed 18; each R is as defined hereinbefore.

Polyazamacrocycles useful as starting materials which can be derivatized to form the cyclic aminophosphonates of Formula III of the present invention include 1,4,7-triazacyclononane, 1,4,7,10-tetraazacyclododecane, 1,4,8,11-tetraazacyclotetradecane, 1,4,7,10,13-pentaazacyclopentadecane, 1,4,7,10,13,16-hexaazacyclooctadecane, and the like. These polyazamacrocycles may be prepared by documented methods such as T. J. Atkins et al., *J. Amer. Chem. Soc.*, 96, 2268-70 (1974) and T. J. Richman et al., *Org. Synthesis*, 58, 86-98 (1978). The preferred starting material, 1,4,7,10-tetraazacyclododecane, for polyazamacrocycles of Formula III is commercially available. Derivatization of the polyazamacrocycles means the reaction of the amine with the appropriate reactive compound to give an R group as defined hereinbefore.

Polyazamacrocycles useful as starting materials for the cyclicaminophosphonates of Formula IV of the present invention are prepared by the procedures set forth in U.S. patent application Ser. No. 07/805,551, filed Dec. 10, 1991, filed on even date herewith and entitled "Bicyclopolyazamacrocyclophosphonic Acids, and Complexes and Conjugates Thereof for Use as Contrast Agents", by Garry E. Kiefer, Jamie Simon and Joseph R. Garlich, the disclosure of which is hereby incorporated by reference. In general, compounds of Formula IV are synthesized by the following reaction scheme.

(5)

Aminophosphonic acids can be prepared by a number of known synthetic techniques. Of particular importance is the reaction of a compound containing at least one reactive amine hydrogen with a carbonyl compound (aldehyde or ketone) and phosphorous acid or derivative thereof as described in U.S. Pat. No. 3,288,846, the disclosure of which is hereby incorporated by reference, and described by Moedritzer and Irani, J. Org. Chem., 31, 1603 (1966). For example, p-nitrobenzyl ethylenediamine reacted with formaldehyde and phosphorous acid can be converted to the p-nitrobenzyl ethylenediaminetetramethylenephosphonic acid. Reduction of the nitro group would yield p-aminobenzyl ethylenediaminetetramethylenephosphonic acid. The preparation of cyclic aminophosphonates of Formula III of the present invention can also be found in U.S. patent application Ser. No. 07/284,876, the disclosure of which is hereby incorporated by reference. In a preferred embodiment of the present invention, all the R substituents of Formulae I-IV are methylene phosphonic acid.

Carboxymethylation of the amines of the present invention may be performed by the method of Desreux using bromoacetic acid derivatives and a suitable base [J. F. Desreux, Inorg. Chem. 19, 1319-24 (1980)].

Methods for carboxyalkylating to give amine derivatives containing a carboxyalkyl group are well known, see, for example, U.S. Pat. No. 3,726,912, the disclosure of which is hereby incorporated by reference, as are the methods which give alkyl phosphonic and hydroxyalkyl substituents on the amine nitrogens, see, for example U.S. Pat. No. 3,398,198, the disclosure of which is hereby incorporated by reference.

While not wishing to be bound by theory, it is believed that the advantageous results of the present invention are obtained because the phosphonomethylene amines act as antinucleating agents inhibiting the formation of crystalline hydroxyapatite from amorphous hydroxyapatite. When used in an oral composition, the cyclic alkylmethylene amines and cyclic methylene amines of the present invention are typically present in a concentration of from about 0.5 millimolar (mM) to about 20 mM, preferably in the range of about 1 mM to about 10 mM, and more preferably about 1 mM to about 2 mM.

In certain highly preferred forms of the invention, the oral compositions are substantially liquid in character, such as a mouthwash or rinse. In such a preparation the vehicle is generally water or a water-alcohol mixture. When alcohol is present, the weight ratio of water to alcohol is in the range of from about 1:1 to about 20:1, preferably about 3:1 to 10:1, and more preferably about 4:1 to about 6:1. The total amount of water or water-alcohol mixture in this type of preparation is typically in the range of from about 70 percent to about 99.9 percent by weight of the preparation.

The pH of such liquid and other preparations of the invention is generally in the range of from about 4.5 to about 9 and typically from about 5.5 to about 8. The pH is preferably in the range of from about 6 to about 8.

A variety of other ingredients may be added to the dentifrices of the present invention. Thus, for example, prophylactic agents, polishing agents, soaps or detergents, flavoring and sweetening agents, thickening agents and humectants may be included using techniques which are known to the art.

In certain other desirable forms of this invention, the oral composition may be substantially solid or semisolid in character, such as toothpowder, a dental tablet, a toothpaste, gel or dental cream. The vehicle of such solid or semisolid oral preparations generally contains added polishing material more fully described hereinafter.

Representative prophylactic agents include supplemental caries-preventing materials such as sodium fluoride, stannous fluoride, potassium fluoride, hexylamine hydrofluoride, myristylamine hydrofluoride, betaine fluoride, glycine potassium fluoride, etc. A particularly preferred fluoride is sodium fluoride. Typically, these prophylactic agents are present in sufficient concentrations so as to provide an available fluoride ion concentration of up to about 2 percent by weight, and preferably in the range of about 0.5-2 percent by weight, of the dentifrice composition.

Suitable polishing agents include, for example, abrasive materials such as insoluble condensed phosphates such as calcium pyrophosphate, insoluble calcium polyphosphate (also known as calcium polymetaphosphate) and highly polymerized sodium polyphosphate; and water impervious cross-linked thermosetting resins. Other suitable polishing agents will be obvious to those skilled in the art.

The polishing material is generally present in the solid or pasty compositions in weight concentrations from about 10 percent to about 99 percent. Preferably, it is present in amounts ranging from about 20 percent to about 75 percent in toothpaste, and from about 70 percent to about 99 percent in tooth powder.

Soaps or detergents may also be employed in the present invention to lower the surface tension to achieve increased prophylactic action, assist in achieving thorough and complete dispersion of the anticalculus agent and render the instant compositions more cosmetically acceptable. Suitable soaps include, for example, the soaps of high molecular weight fatty acids such as sodium and potassium soaps of myristic, stearic or palmitic acids and fatty acids mixtures of palm oil and coconut oil. Typical synthetic detergents include alkyl sulfates and sulfonates having alkyl groups of from about 8 to about 18 carbon atoms, such as sodium lauryl sulfate, the sulfated fatty alcohols derived from coconut oil, palm oil, and the like. The soaps typically comprise up to about 5 percent by weight of the dentifrice composition.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine, APM (aspartyl phenylalanine, methyl ester), saccharine and the like. Suitably, flavor and sweetening agents may together comprise from about 0.1 percent to 5 percent of the preparation.

Toothpastes, creams and gels typically contain a natural or synthetic thickener or gelling agent in proportions from about 0.1 to about 10 percent, preferably about 0.5 to about 5 percent, by weight. Suitable gelling or thickening agents include for example, water-soluble salts of cellulose ethers such as sodium carboxymethyl cellulose and sodium carboxymethyl hydroxy ethyl cellulose; natural gums such as gum karaya, gum arabic, and gum tragacanth; and colloidal magnesium aluminum silicate or finely divided silica.

Suitable humectants which may be employed in compositions of the invention include glycerine, propylene glycol, sorbitol, polypropylene glycol and/or polyethylene glycol and other polyhydric alcohols. The humectants may comprise 10 to 90 percent by weight of the dentifrice composition.

It has also been surprisingly found that in the presence of a cyclic alkylamine or cyclic amine of the present invention, the inclusion of a cationic antimicrobial compound in the dentifrice results in the antimicrobial compound being retained in the oral cavity for a longer period of time than in the absence of a cyclic alkylamine or cyclic amine. While not wishing to be bound by theory, it is believed that the cyclic alkylamines and cyclic amines of the present invention have an affinity for the tooth surface creating an anionic surface on the teeth to which cationic antimicrobial compounds are beneficially attracted. The antimicrobial is therefore retained within the oral cavity for alonger period of time due to the electrostatic forces between the anionic tooth surface and the cationic antimicrobial. The ability of an antimicrobial compound to be retained and remain active within the oral cavity to exert an antiplaque effect for a longer period of time is referred to as the "substantivity" of the compound. The terms "antimicrobial" and "antibacterial" as used herein refer to the ability of a cationic compound to inhibit the growth, reproduction or metabolism of microorganisms.

The enhanced substantivity of the antimicrobial compound aids in the prevention of dental calculus by inhibiting microorganisms responsible for the initial formation of dental plaque. The inhibition of microorganisms will also reduce the amount of volatile sulfur compounds produced by the putrefactive activity of the microorganisms, thus helping to control mouth malodor. It has also been surprisingly found that inclusion of an antimicrobial does not affect the calculus inhibiting ability of the cyclic alkylamines or cyclic amines used in the dentifrices of the present invention.

Antimicrobial compounds which are particularly useful in dentifrice compositions of the present invention are compounds which contain an organic amine where the nitrogen is capable of being positively charged in an aqueous environment, preferably organic amines which are capable of being protonated in an aqueous environment and quaternary ammonium compounds.

Among the most common antibacterial quaternary ammonium compounds used in oral compositions are cetylpyridinium chloride and benzethonium chloride, also known as Hyamine 1622 or di-isobutyl(phenoxyethoxyethyl dimethylbenzyl ammonium chloride). Antibacterial quaternary ammonium compounds useful in the present invention include those represented by the formula (V)

and formula

(VI)

wherein
$R^1$ is a $C_8$–$C_{20}$ alkyl;
$R^2$ is benzyl or $C_1$–$C_{12}$ alkyl;
$R^3$ and $R^4$ are independently a $C_1$–$C_7$ alkyl or —(CH$_2$—CHOH—CH$_2$—O)$_n$H wherein n is 1 to 6;
$R^5$ is —H, a $C_1$–$C_7$ alkyl or —(CH$_2$—CHOH—CH$_2$—O)$_n$H wherein n is an integer from 1 to 6; and
$X^-$ is chloride (Cl$^-$), bromide (Br$^-$), iodide (I$^-$) or fluoride (F$^-$).

The quaternary ammonium compounds useful in the present invention are commercially available or may be obtained by those of ordinary skill in the art without undue experimentation. For example, they may be produced by reacting alkyl halides with ammonia or primary amines, or by reacting a tertiary amine, pyridine or pyridine derivative with an alkyl halide. See, for example, Zoltewicz and Deady, Adv. Heterocycl. Chem., 22, 71-121 (1978); U.S. Pat. Nos. 2,446,792; 2,295,504 and 4,994,199, the teachings of which are hereby incorporated by reference.

Other quaternary ammonium compounds which can be employed in dentifrices of the present invention include the following:

Pyridinium chlorides containing alkylthiomethyl or alkoxymethy hydrophobic groups as disclosed by Weglowski et al., J. Phar. Sci., 80, 91-85 (1991), the disclosure of which is hereby incorporated by reference, the quaternary ammonium compounds having the formula wherein
X is as defined herein before and $X^1$ is oxygen or sulfur; and
$R^6$ is a $C_4$–$C_{16}$ alkyl or benzyl.

Quaternary ammonium compounds that are esters of betaine and fatty alcohols, as disclosed by Linstedt et al., Antimicrobial Agents and Chemotherapy, 39, 1949-1954 (1990), the disclosure of which is hereby incorporated by reference, the quaternary ammonium compounds having the formula $(CH_3)_3N^{\oplus}$—$CH_2C(O)OR^7$;

wherein $R^7$ is a $C_{10}$–$C_{18}$ alkyl; and physiologically acceptable salts thereof.

Sanguinarine and sanguinaria, sanguinaria being an extract from the bloodroot plant *Sanguinaria candensis*, the extract containing benzophenanthridine alkaloids such as sanguinarine, chelerythrine, protopine, homochelidonine and physiologically acceptable salts thereof as disclosed in U.S. Pat. Nos. 4,145,412 and 4,406,881, the disclosures of which are hereby incorporated by reference. Sanguinaria is available in dentifrices under the trademark Viadent TM brand sanguinaria; the major active ingredient sanguinarine chloride salt having the formula Dodecyltrimethylammonium bromide, benzyl dimethylstearylammonium chloride, cetylpyridinium chloride, N-tetradecyl-4-ethylpyridinium chloride, sanguinaria and 5-amino-1,3,bis(2-ethyl-hexyl)-5-methylhexahydropyrimidine are preferred quaternary ammonium antibacterial agents used in dentifrices of the present invention.

Examples of antibacterial organic amines which can be protonated in aqueous environments and are useful in dentifrices of the present invention include the following:

Morpholine compounds as disclosed in U.S. Pat. No. 4,894,221, the disclosure of which is hereby incorporate by reference, the morpholine compounds having the formula wherein
  $R^8$ is a $C_8$–$C_{16}$ alkyl at the 2 or 3 position of the morpholino ring;
  $R^9$ is a $C_2$–$C_{10}$ alkyl substituted with a hydroxy group at other than the alpha-position;
  the sum of $R^8$ and $R^9$ being greater than or equal to 10 and preferably 10–20; and physiologically acceptable salts thereof.

Antibacterial secondary amines and amides as disclosed in *J. Antibacterial and Antifungal Agents*, 17, 371 (1989), the disclosure of which is hereby incorporated by reference, wherein the antibacterial compounds have the following formula wherein $R^{10}$ is a $C_{10}$–$C_{18}$ alkyl;

wherein each $R^{11}$ is independently $C_8H_{17}$ or $C_{10}H_{21}$;

wherein $R^{13}$ is a $C_9$–$C_{17}$ alkyl;

wherein each $R^{13}$ is independently $C_7H_{15}$ or $C_9H_{19}$; and physiologically acceptable salts thereof.

Dialkyl amines and N,N'-dialkylpolymethylenediamines as disclosed in *J. Antibacterial and Antifungal Agents*, 17, 579 (1989), the disclosure of which is hereby incorporated by reference, having the formula wherein each $R^{14}$ is independently $C_8H_{17}$ or $C_{12}H_{25}$; or formula wherein each $R^{15}$ is independently a $C_7$–$C_{10}$ alkyl;
  n is an integer from 2 to 5; and pharmaceutically acceptable salts thereof.

N'-Alkyl-N-(2-aminoethyl)piperidine compounds as disclosed by Murata et al., *J. Pharm. Sci.*, 80, 26–28 (1991), the disclosure of which is hereby incorporated by reference, the compounds having the formula wherein $R^{16}$ is a $C_{10}$–$C_{18}$ alkyl; and pharmaceutically acceptable salts thereof.

The ammonium compound 4-(2-propylenepentyl)-1-piperidinoethanol having the structure wherein $X^-$ is as defined hereinbefore. This antimicrobial is described in *J. Periodontal Research*, 18, pp. 429–437 (1983), as Octapinal TM brand 4-(2-propylenepentyl)-1-piperidinoethanol (Ferrosan AB, Sweden).

Alkyl-N-betaine in combination with an alkyl-N,N-dimethylamine oxide; the alkyl-N-betaine having the structure wherein R$^{17}$ is a C$_{10}$–C$_{18}$ alkyl;
the alkyl-N,N-dimethylamine having the structure wherein R$^{18}$ is a C$_{10}$–C$_{18}$ alkyl;
as disclosed in U.S. Pat. No. 4,839,158, the disclosure of which is hereby incorporated by reference.

Other antimicrobial agents which can be employed in the dentifrices of the present invention include
biguanides such as chlorhexidine (1,6-bis[N$^5$-(p-chlorophenyl)-N'biguanido]hexane;
N'-(4-chlorobenzyl)-N$^5$-(2,4-dichlorobenzyl)biguanide;
p-chlorophenyl biguanide;
4-chlorobenzylhydrylbiguanide;
N-3-lauroxypropyl-N$^5$-p-chlorobenzylbiguanide;
5,6-dichloro-2-guanidinobenzimidazole;
N'-p-chlorophenyl-N$^5$-laurylbiguanide;
and their non-toxic acid addition salts. Chlorhexidine being the preferred biguanide antimicrobial agent used in the dentifrices of the present invention.

The antibacterial agents are typically employed in amounts such that the oral product contains from about 0.001 percent to about 15 percent by weight of the agent. Preferably for desired levels of antiplaque effect, the finished oral product contains from about 0.01 percent to about 5 percent and most preferably from about 0.025 percent to 1.0 percent by weight of the agent.

The dentifrices of the present invention may also be in a kit form, the kit comprising in a first compartment an orally-acceptable vehicle containing one or more cyclic alkylamines or cyclic amines and in a second compartment an orally-acceptable vehicle containing one or more cationic antimicrobial compounds. When the dentifrice is in a kit form, the compounds in the separate compartments may be applied to the oral cavity sequentially or mixed prior to application. When applied sequentially, it is preferred that the cyclic alkyl amine or cyclic amine be applied to the oral cavity prior to the cationic antimicrobial compounds.

When mixing the cyclic alkylamine or cyclic amine with the cationic antimicrobial compound prior to application to the oral cavity, it may be necessary to increase their concentration to account for dilution effects which can occur upon mixing. Whether applying the cyclic alkylamine or cyclic amine and cationic antimicrobial compound sequentially or mixing prior to use, the concentration of the cyclic alkylamine, cyclic amine and cationic antimicrobial compound to which the oral cavity is exposed should be in the range given hereinbefore for their concentration in the final dentifrice product. For ease of use, it is desirable for the dentifrice to contain both the antimicrobial and cyclic alkylamine or cyclic amine in one composition.

A variety of other ingredients may be added to the separate compartment of a dentifrice kit, such as, polishing agents, soaps or detergents, flavoring and sweetening agents, and the like as described hereinbefore.

It has also been surprisingly found that inclusion of a polyvalent metal ion, such as calcium (Ca$^{2+}$), magnesium (Mg$^{2+}$) or mixtures thereof with a cyclic amine or with a cyclic amine and antimicrobial compound, does not interfere with the ability of the cyclic amine to inhibit calculus formation. The molar ratio of the metal ion to cyclic amine is preferably from about 5:1 to about 1:5, more preferably from about 3:1 to 1:3, and most preferably about 1:1.

In the practice of this invention, an oral composition according to this invention, such as a mouthwash or tooth paste containing the cyclic alkylamine or cyclic amine, and/or a cationic antimicrobial compound and/or a metal ion, may be prepared by unifying the components in conventional manner and applied to the teeth and gingiva using customary procedures for oral care.

The invention will be further clarified by a consideration of the following examples, which are intended to be purely exemplary of the present invention.

GLOSSARY

DCDATMP = dicyclopentadienediaminetetramethylenephosphonic acid
DOTMP = 1,4,7,10-tetraazacyclododecane-1,4,7,10-tetramethylenephosphonic acid
DTPMP = diethylenetriaminepentamethylenephosphonic acid
EDTMP = ethylenediaminetetramethylenephosphonic acid
HAP = hydroxyapatite
HEDP = hydroxyethylidenediphosphonic acid
NDATMP = norbornanediaminetetramethylenephosphonic acid
PCTMP = 3,6,9,15-tetraazabicyclo[9.3.1]pentadeca-1(15),11,13-triene-3,6,9-trimethylenephosphonic acid
NOTMP = 1,4,7-triazanonanetrimethylenephononic acid Preparation of Stock Solutions 0.0045M DOTMP. A stock solution of 0.0045 molar (M) 1,4,7,10-tetraazacyclododecane-1,4,7,10-tetramethylenephosphonic acid (DOTMP) was prepared by adding 0.6168±0.0001 g of solid DOTMP to a 60 mL beaker and brought into solution with the addition of 20 mL of water and the dropwise addition of 1.0N sodium hydroxide solution to raise the pH of the solution to 7.4. This solution was transferred quantitatively to a 250 mL volumetric flask and diluted to mark with water.

0.0015M DOTMP. Twenty mL of a 0.0045M DOTMP stock solution was loaded into a four ounce jar and then diluted with 40 mL of water to produce a 0.0015M DOTMP solution.

0.0015M HEDP. A 0.0045M solution of HEDP was prepared by adding 40 mL of water of a 60 mL beaker containing 0.0618±0.001 g of 60 percent active HEDP (MAYO Chemical Co., FW 206). This solution was adjusted to pH 7.6 using few drops of 1.0N sodium hydroxide. A 20 mL aliquot of the solution was removed and placed in a four ounce jar where it was diluted with 40 mL of water to produce a 0.0015M HEDP solution.

The procedures for making solutions of EDTMP, HEDP, NDATMP, DCDATMP, DTPMP, PCTMP and NOTMP were done in a similar manner.

Crystal Growth Inhibition Determination

The efficacy of the compositions of this invention in calculus prophylaxis was demonstrated by crystal growth inhibition tests. Inhibition of HAP formation was evaluated by a pH stat method, the procedure being as follows:

To 50 mL of water in a 100 mL disposable beaker was added 2.0 mL of 0.1M phosphate solution ($KH_2PO_4$, adjusted to pH 7.4 with NaOH). An inhibitor, if desired, was added, typically 10 to 30 microliters ($\mu L$) of a 0.09M solution. The beaker was secured to an automatic titrator and stirring begun. A constant temperature water bath was raised around the beaker to keep the temperature of the reaction constant at 25° C. After stirring for several minutes to allow for temperature equilibration, the run was started by the addition of 2.0 mL of a 0.175M calcium solution ($CaCl_2 \cdot 2H_2O$, pH 7.4). A pH stat titration was immediately begun, keeping the pH at about 7.4 by the addition of 0.01M NaOH when needed. The volume of titrant consumed versus time during the run was recorded. Runs were typically stopped after one hour.

An initial rise in titrant consumption was observed due to the formation of amorphous calcium phosphate. A later rise in titrant consumption (approximately 22 minutes in the control) was due to the formation of hydroxyapatite. The presence of inhibitors delays or prevents this second rise in titrant consumption.

EXAMPLE 1

Figure 1:
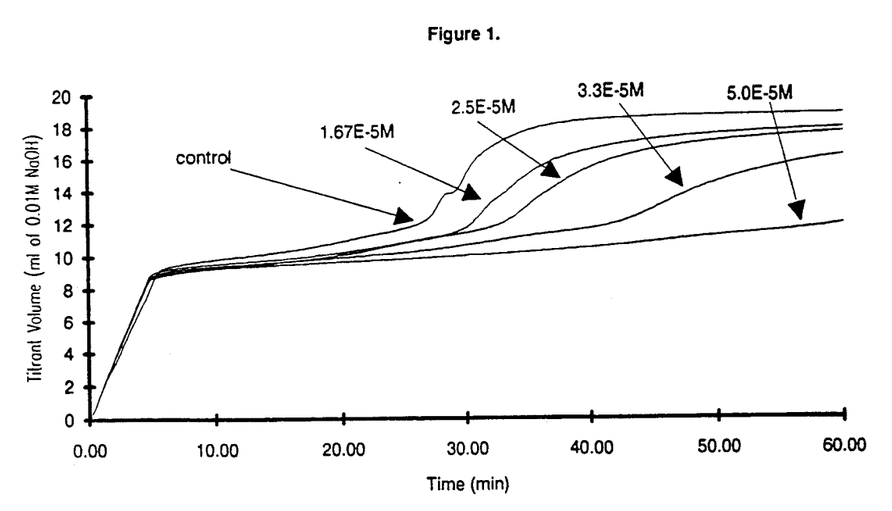
FIG. 1 shows the inhibition of hydroxyapatite formation as observed by a decrease in the amount of titrant consumed in the presence of various concentrations of ethylenediaminetetramethylenephosphonic acid (EDTMP).
Figure 2:
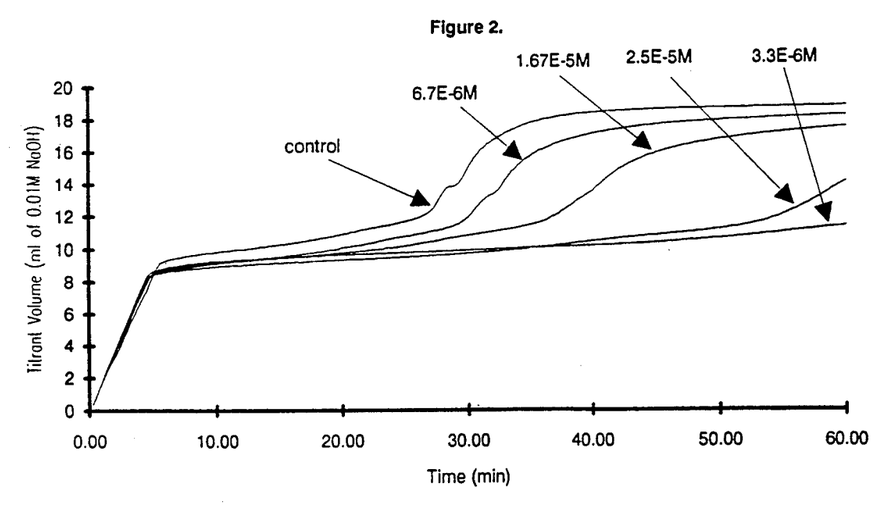
FIG. 2 shows the inhibition of hydroxyapatite formation as observed by a decrease in the amount of titrant consumed in the presence of various concentrations of 1,4,7,10-tetraazacyclododecane-1,4,7,10-tetramethylenephosphonic acid (DOTMP).

Using the above pH stat procedure, two inhibitors, ethylenediaminetetramethylenephosphonic acid (EDTMP) and 1,4,7,10-tetraazacyclodocecane-1,4,7,10-tetramethylenephosphonic acid (DOTMP) were each evaluated at various levels and compared to a control. Both inhibitors were prepared as 0.09M solutions of the ammonium salts. Levels of EDTMP used were 10, 15, 20, and 30 $\mu L$. Levels of DOTMP used were 4, 10, 15, 20 $\mu L$ (20 $\mu L$ in 54 mL equals $3.3 \times 10^{-5}$M, or on a weight basis, 14.5 ppm of EDTMP and 18.3 ppm of DOTMP). As can be seen from the FIGS. 1 and 2, 4 $\mu L$ of DOTMP is equivalent to 10 $\mu L$ of EDTMP.

EXAMPLE 2

Figure 3:
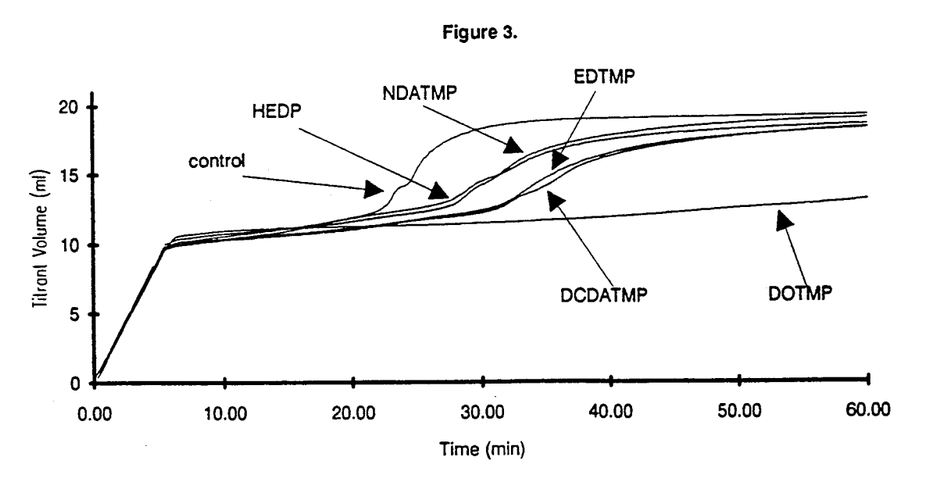
FIG. 3 shows the inhibition of hydroxyapatite formation as observed by a decrease in the amount of titrant consumed in the presence of $3.3 \times 10^{-5}$M DOTMP, hydroxyethylidenediphosphonic acid (HEDP), EDTMP, norbornanediaminetetramethylenephosphonic acid (NDATMP), or dicyclopentadienediaminetetramethylenephosphonic acid (DCDATMP).

Using the above pH stat procedure, six inhibitors, all at $3.3 \times 10^{-5}$M (20 $\mu L$ of a 0.09M solution in 54 mL) were tested against water as a control. They are, in order of increasing efficacy, HEDP, NDATMP, EDTMP, DCDATMP, DTPMP and DOTMP. As can be seen from FIGS. 2 and 3, DOTMP stands out as the best HAP scale inhibitor.

EXAMPLE 3

Figure 4:
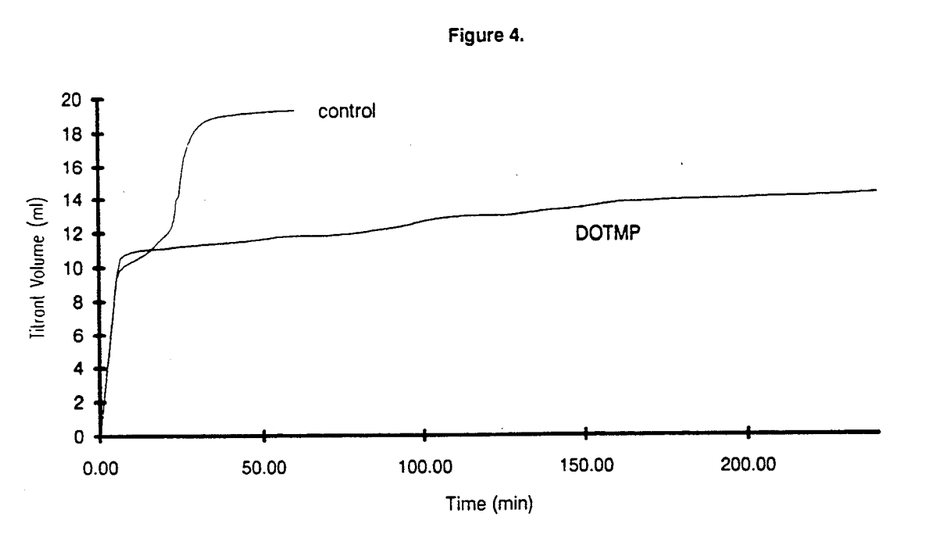
FIG. 4 shows the inhibition of hydroxyapatite formation as observed by a decrease in the amount of titrant consumed in the presence of $3.3 \times 10^{-5}$M DOTMP over a 4 hour time period.

Using the above pH stat procedure, an extended run (4 hours) was made with DOTMP at the $3.3 \times 10^{-5}$M level (20 $\mu L$ of a 0.09M solution in 54 mL). As can be seen from FIG. 4, there is no appreciable HAP formation even at 4 hours.

EXAMPLE 4

Figure 5:
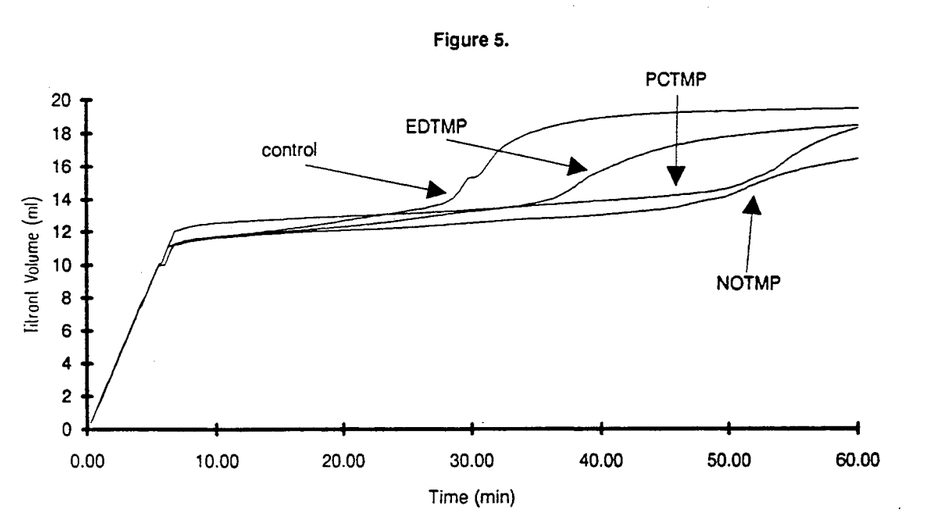
FIG. 5 shows the inhibition of hydroxyapatite formation as observed by a decrease in the amount of titrant consumed in the presence of $2.71 \times 10^{-5}$M EDTMP, 3,6,9,15-tetraazabicyclo[9.3.1]tetradeca-1-(15),-11,13-triene-3,6,9-trimethylenephosphonic acid (PCTMP) or 1,4,7-triazacyclononanetrimethylenephosphinic acid (NOTMP).

Using the above pH stat procedure, the inhibitors EDTMP, PCTMP and NOTMP all at $2.71 \times 10^{-5}$M, were tested against water as a control. The results of this trial are shown in FIG. 5.

EXAMPLE 5

Figure 6:
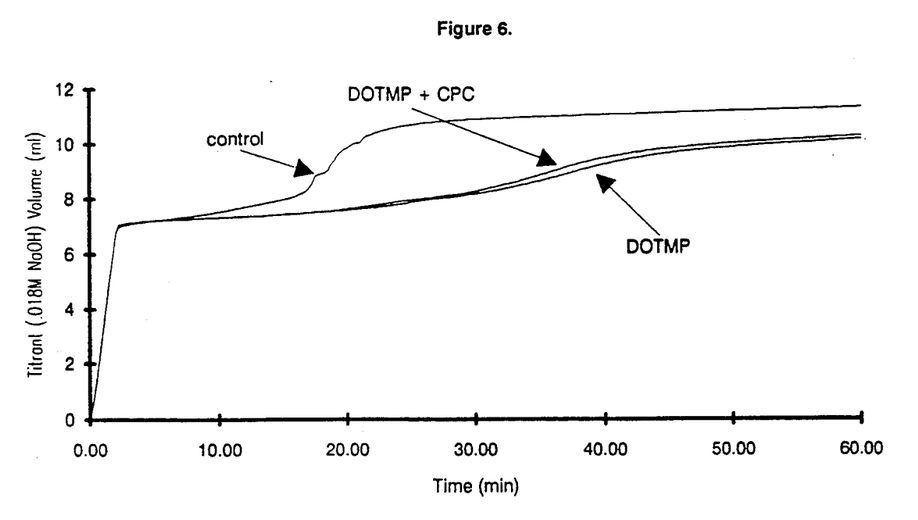
FIG. 6 shows the inhibition of hydroxyapatite formation as observed by a decrease in the amount of titrant consumed in the presence of $2.73 \times 10^{-5}$M DOTMP and DOTMP plus cetylpyridinium chloride (CPC) both present at a $2.73 \times 10^{-5}$M concentration.

Using the above pH stat procedure, the effect of adding an equal molar concentration of cetylpyridinium chlorice (CPC) to the inhibitor DOTMP was determined. As can be seen from FIG. 6, the addition of an equal molar amount of CPC to DOTMP (both at $2.73 \times 10^{-5}$M) did not substantially inhibit the ability of DOTMP ($2.73 \times 10^{-5}$M) to prevent hydroxyapatite formation.

EXAMPLE 6

Using the above pH stat procedure, adding an equal molar amount of magnesium or calcium ion to a $3.3 \times 10^{-5}$M solution of DOTMP did not inhibit the ability of DOTMP to prevent hydroxyapatite formation.

EXAMPLE 5

An in-vivo study was conducted to determine the ability of formulations containing DOTMP to inhibit formation of experimental dental calculus in Beagle dogs.

Purebred female Beagle dogs, 2-3 years old, with naturally occurring gingivitis were randomly divided into groups of four animals each. After 14 days of adaptation, the teeth of the dogs were scaled to remove supragingival calculus and polished. One week following the prophylaxis, during which time oral care was maintained by brushing, a baseline calculus index measurement as measured by the procedure of H. Loe, *J. Periodontol*. 38, 610 (1967) was taken. After the initial calculus index reading, the teeth of each group were sprayed twice daily, five days per week, with approximately 10 mL of one of the following mouth rinses:

(A) 0.0015M cetylpyridinium chloride (CPC);
(B) 0.0015M DOTMP, 0.015M CPC (DOTMP/CPC);
(C) 0.0015M stannous, 0.015M DOTMP (Sn-DOTMP); or
(D) 0.0015M calcium, 0.015M DOTMP (Ca-DOTMP).

The CPC solution was prepared by dissolving 1.096 g of cetylpyridinium chloride in 2.0 liters of water.

The DOTMP/CPC solution was prepared by adding 1.674 g of DOTMP to 50 mL of water and dissolving with the addition of 50% by weight sodium hydroxide to raise the pH to about 7.0. This solution was then added to 1.096 g of cetylpyridinium chloride dissolved in 30 mL of water. This solution was then diluted to 2.0 liters with the final pH being about 7.66.

To prepare the solutions containing the stannous or calcium, DOTMP was prepared as above and added to 30 mL of water containing 0.419 g of calcium chloride dihydrate or 0.477 g stannous fluoride. The solutions were then diluted to a total volume of 2 liters.

After four weeks of treatment, the calculus index was again measured. The results given in Table I, show that the Ca-DOTMP composition was the most effective composition of those tested for preventing an increase in calculus index.

TABLE I

| Formulation* | Increase in Calculus Index over 4 weeks |
|---|---|
| (A) CPC | 0.295 |
| (B) DOTMP/CPC | 0.209 |
| (C) Sn-DOTMP | 0.158 |

TABLE I-continued

| Formulation* | Increase in Calculus Index over 4 weeks |
|---|---|
| (D) Ca-DOTMP | 0.127 |

*CPC = cetylpyridinium chloride;
DOTMP = 1,4,7,10-tetraazadodeane-1,4,7,10-tetramethylene phosphonic acid;
Sn = tin;
Ca = calcium Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. An oral composition consisting essentially of an orally-acceptable vehicle containing therein an effective amount as an anticalculus agent one or more of dicyclopentadienediaminetetramethylenephosphonic acid; 1,4,7,10-tetraazacyclododecane-1,4,7,10-tetramethylenephosphonic acid; diethylenetriaminepentamethylenephosphonic acid; norbornanediaminetetramethylenephosphonic acid; 3,6,9,15-tetraazabicyclo(9.3.1)pentadeca-1(15), 11,13-triene-3,6,9-trimethylenephosphonic acid; 1,4,7-triazanonanetrimethylenephosphonic acid, or physiologically acceptable salts thereof.

2. The oral composition of claim 1 wherein the anticalculus agent is present in a concentration from about 0.5 millimolar to about 20 millimolar.

3. The oral composition of claim 1 wherein the physiologically acceptable salt is a magnesium or calcium salt, or a mixture thereof.

4. A method of inhibiting the formation of dental calculus comprising administering to the oral cavity a calculus inhibiting amount of an oral composition containing an effective amount as an anticalculus agent one or more of dicyclopentadienediaminetetramethylenephosphonic acid; 1,4,7,10-tetraazacyclododecane-1,4,7,10-tetramethylenephosphonic acid; diethylenetriaminepentamethylenephosphonic acid; norbornanediaminetetramethylenephosphonic acid; 3,6,9,15-tetraazabicyclo-(9.3.1)pentadeca-1(15), 11,13-triene-3,6,9-trimethylenephosphonic acid; or 1,4,7-triazanonanetrimethylenephosphonic acid.

5. The method of claim 4 wherein the anticalculus agent is present in a concentration from about 0.5 millimolar to about 20 millimolar.

6. The method of claim 4 wherein the physiologically acceptable salt is a calcium or magnesium salt, or a mixture thereof.

* * * * *